United States Patent [19]

Krief et al.

[11] Patent Number: 5,612,195
[45] Date of Patent: Mar. 18, 1997

[54] RECOMBINANT PRODUCTION OF A HUMAN INTERFERON (IFN)-GAMMA ANTAGONIST CYTOKINE

[75] Inventors: Patricia Krief, Gonesse; Bruno Azzarone, Longjumeau; Yvette Augery-Bourget, Paris; Claude Boucheix, Villejuif; Claude Jasmin, Paris, all of France

[73] Assignee: Institut National de la Sante et de la Recherche Medicale (INSERM), Paris, France

[21] Appl. No.: 244,557

[22] PCT Filed: Feb. 12, 1992

[86] PCT No.: PCT/FR92/01123

§ 371 Date: Aug. 29, 1994

§ 102(e) Date: Aug. 29, 1994

[87] PCT Pub. No.: WO93/11232

PCT Pub. Date: Jun. 10, 1993

[30] Foreign Application Priority Data

Dec. 2, 1991 [FR] France .................................. 91 14908

[51] Int. Cl.[6] .......................... C12N 15/19; A61K 38/19; C07K 14/52

[52] U.S. Cl. ................ 435/69.5; 435/252.3; 435/254.11; 435/320.1; 435/325; 435/365.1; 536/23.51; 536/24.31; 536/23.5; 530/350; 530/351; 424/85.1

[58] Field of Search .................................... 530/350, 351; 424/85.1; 536/23.5, 23.51, 24.31; 435/69.5, 240.2, 252.3, 254.11, 320.1

[56] References Cited

U.S. PATENT DOCUMENTS 5,461,033 10/1995 Donnet et al. ............................ 514/12

FOREIGN PATENT DOCUMENTS 9105799 5/1991 WIPO .

OTHER PUBLICATIONS

Hofer, E. (1987) Gen Bank database record, acc. No. Y00083.

European Journal of Immunology, vol. 17, No. 7, 1987, Weinheim; DE. pp. 1021–1025.

Proceedings of the American Association for Cancer Research Annual Meeting, vol. 29, p. 80, Mar. 1988, New Orleans, Louisiana; US Abst. No. 318.

Biological Abstracts, vol. 88, No. 1, 1989, pp. 413–656, abst. No. 6547.

*Primary Examiner*—Stephen G. Walsh
*Assistant Examiner*—David L. Fitzgerald
*Attorney, Agent, or Firm*—Blakely, Sokoloff, Taylor & Zafman LLP

[57] ABSTRACT

A cytokine that is a specific antagonist of induction by interferon-gamma of the expression of class II histocompatibility antigens at the cell surface is disclosed. The cytokine is naturally secreted by cells or is the expression product of an exogenous DNA sequence in prokaryotic or eukaryotic cells. Also disclosed is a DNA sequence that codes, on expression in a host cell, for a cytokine having a biological activity that is a specific antagonist of induction by interferon-gamma of the expression of class II histocompatibility antigens at the cell surface. A method for preparing the cytokine is further disclosed. Finally, a therapeutic composition containing the cytokine is disclosed.

13 Claims, 6 Drawing Sheets

```
                                      v        v       v      v
                              cgggggaagctggaagagaagaaacctcctgaggctgac         39
    v           v          v            v          v          v
atgaatattttgaagacattggggattacgtaccctccacaaccaagacacctcgggac                   99
MetAsnIlePheGluAspIleGlyAspTyrValProSerThrThrLysThrProArgAsp                  30
    v          v          v           v          v          v
aaggagcgggagagatatcgggaacgggagcgtgatcgggaaagagacagagaccgtgac                 159
LysGluArgGluArgTyrArgGluArgGluArgAspArgGluArgAspArgAspArgAsp                  40
    v          v          v           v          v          v
cgagagcgagagcgagaacgagatcgggaacgagagcgagagcgggaccgagagagagaa                 219
ArgGluArgGluArgGluArgAspArgGluArgGluArgGluArgAspArgGluArgGlu                  60
    v          v          v           v          v          v
gaggaaaagaagagacacagctactttgagaagccaaaagtagatgatgagcccatggac                 279
GluGluLysLysArgHisSerTyrPheGluLysProLysValAspAspGluProMetAsp                  80
    v          v          v           v          v          v
gttgacaaaggacctgggtctaccaaggagttgatcaagtccatcaatgaaaagtttgct                 339
ValAspLysGlyProGlySerThrLysGluLeuIleLysSerIleAsnGluLysPheAla                 100
    v          v          v           v          v          v
gggtctgctggctgggaaggcacagaatcgctgaagaagccagaagacaaaaagcagctg                 399
GlySerAlaGlyTrpGluGlyThrGluSerLeuLysLysProGluAspLysLysGlnLeu                 120
    v          v          v           v          v          v
ggagatttctttggcatgtccaacagttatgcagagtgctacccagccacgatggatgac                 459
GlyAspPhePheGlyMetSerAsnSerTyrAlaGluCysTyrProAlaThrMetAspAsp                 140
    v          v          v           v          v          v
atggctgtggatagtgatgaggaggtggattatagcaaaatggaccagggtaacaagaag                 519
MetAlaValAspSerAspGluGluValAspTyrSerLysMetAspGlnGlyAsnLysLys                 160
    v          v          v           v          v          v
ggcccttagggccgttgggactttgatacccaggaagaatacagcgagtatatgaacaac                 579
GlyProTer       162
    v          v          v           v          v          v
aaagaagctttgcccaaggctgcattccagtatggtatcaaaatgtctgaagggcggaaa                 639
    v          v          v           v          v          v
accaggcgcttcaaggaaaccaatgacaaagcagagcttgatcgccagtggaagaagatt                 699
    v          v          v           v          v          v
agtgcaatcattgagaagaggaagaagatggaagctgatggggttgaagtcaagccg                    756
```

FIG. Ia

Analysis of the composition of the FKI protein    From 1 to 162

| Amino acid | | |
|---|---|---|
| Ala | 5 | 3.09 |
| Cys | 1 | 0.62 |
| Asp | 21 | 12.96 |
| Glu | 26 | 16.05 |
| Phe | 5 | 3.09 |
| Gly | 10 | 6.17 |
| His | 1 | 0.62 |
| Ile | 4 | 2.47 |
| Lys | 17 | 10.49 |
| Leu | 3 | 1.85 |

Amino acid composition
Total residues 162

| Amino acid | Deduced | Mol% |
|---|---|---|
| Met | 6 | 3.70 |
| Asn | 4 | 2.47 |
| Pro | 8 | 4.94 |
| Gln | 2 | 1.23 |
| Arg | 21 | 12.96 |
| Ser | 10 | 6.17 |
| Thr | 6 | 3.70 |
| Val | 5 | 3.09 |
| Trp | 1 | 0.62 |
| Tyr | 6 | 3.70 |
| Ter | 0 | 0.00 |

Noninterpretable residues  0

Molecular mass of the protein  = 19361.70

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 756 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION:40..528

( x i ) SEQUENCE DESCRIPTION: SEQ ID NO: 1:

```
CGGGGGAAGC  TGGAAGAGAA  GAAACCTCCT  GAGGCTGAC  ATG  AAT  ATT  TTT  GAA         54
                                               Met  Asn  Ile  Phe  Glu
                                                1                    5

GAC  ATT  GGG  GAT  TAC  GTA  CCC  TCC  ACA  ACC  AAG  ACA  CCT  CGG  GAC  AAG   102
Asp  Ile  Gly  Asp  Tyr  Val  Pro  Ser  Thr  Thr  Lys  Thr  Pro  Arg  Asp  Lys
          10                        15                            20
```

| | | | | | | | | | | | | | | | | |
|---|---|---|---|---|---|---|---|---|---|---|---|---|---|---|---|---|
| GAG | CGG | GAG | AGA | TAT | CGG | GAA | CGG | GAG | CGT | GAT | CGG | GAA | AGA | GAC | AGA | 150 |
| Glu | Arg | Glu | Arg | Tyr | Arg | Glu | Arg | Glu | Arg | Asp | Arg | Glu | Arg | Asp | Arg | |
| | | | 25 | | | | | 30 | | | | | 35 | | | |
| GAC | CGT | GAC | CGA | GAG | CGA | GAG | CGA | GAA | CGA | GAT | CGG | GAA | CGA | GAG | CGA | 198 |
| Asp | Arg | Asp | Arg | Glu | Arg | Glu | Arg | Glu | Arg | Asp | Arg | Glu | Arg | Glu | Arg | |
| | | 40 | | | | | 45 | | | | | 50 | | | | |
| GAG | CGG | GAC | CGA | GAG | AGA | GAA | GAG | GAA | AAG | AAG | AGA | CAC | AGC | TAC | TTT | 246 |
| Glu | Arg | Asp | Arg | Glu | Arg | Glu | Glu | Glu | Lys | Lys | Arg | His | Ser | Tyr | Phe | |
| | 55 | | | | | 60 | | | | | 65 | | | | | |
| GAG | AAG | CCA | AAA | GTA | GAT | GAT | GAG | CCC | ATG | GAC | GTT | GAC | AAA | GGA | CCT | 294 |
| Glu | Lys | Pro | Lys | Val | Asp | Asp | Glu | Pro | Met | Asp | Val | Asp | Lys | Gly | Pro | |
| 70 | | | | | 75 | | | | 80 | | | | | | 85 | |
| GGG | TCT | ACC | AAG | GAG | TTG | ATC | AAG | TCC | ATC | AAT | GAA | AAG | TTT | GCT | GGG | 342 |
| Gly | Ser | Thr | Lys | Glu | Leu | Ile | Lys | Ser | Ile | Asn | Glu | Lys | Phe | Ala | Gly | |
| | | | | 90 | | | | | 95 | | | | | | 100 | |
| TCT | GCT | GGC | TGG | GAA | GGC | ACA | GAA | TCG | CTG | AAG | AAG | CCA | GAA | GAC | AAA | 390 |
| Ser | Ala | Gly | Trp | Glu | Gly | Thr | Glu | Ser | Leu | Lys | Lys | Pro | Glu | Asp | Lys | |
| | | | | 105 | | | | | 110 | | | | | 115 | | |
| AAG | CAG | CTG | GGA | GAT | TTC | TTT | GGC | ATG | TCC | AAC | AGT | TAT | GCA | GAG | TGC | 438 |
| Lys | Gln | Leu | Gly | Asp | Phe | Phe | Gly | Met | Ser | Asn | Ser | Tyr | Ala | Glu | Cys | |
| | | 120 | | | | | 125 | | | | | 130 | | | | |
| TAC | CCA | GCC | ACG | ATG | GAT | GAC | ATG | GCT | GTG | GAT | AGT | GAT | GAG | GAG | GTG | 486 |
| Tyr | Pro | Ala | Thr | Met | Asp | Asp | Met | Ala | Val | Asp | Ser | Asp | Glu | Glu | Val | |
| | | 135 | | | | | 140 | | | | | 145 | | | | |
| GAT | TAT | AGC | AAA | ATG | GAC | CAG | GGT | AAC | AAG | AAG | GGC | CCT | TAG | | | 528 |
| Asp | Tyr | Ser | Lys | Met | Asp | Gln | Gly | Asn | Lys | Lys | Gly | Pro | * | | | |
| 150 | | | | | 155 | | | | | 160 | | | | | | |

| | | | | | |
|---|---|---|---|---|---|
| GGCCGTTGGG | ACTTTGATAC | CCAGGAAGAA | TACAGCGAGT | ATATGAACAA | CAAAGAAGCT | 588 |
| TTGCCCAAGG | CTGCATTCCA | GTATGGTATC | AAAATGTCTG | AAGGGCGGAA | AACCAGGCGC | 648 |
| TTCAAGGAAA | CCAATGACAA | AGCAGAGCTT | GATCGCCAGT | GGAAGAAGAT | TAGTGCAATC | 708 |
| ATTGAGAAGA | GGAAGAAGAT | GGAAGCTGAT | GGGGTTGAAG | TCAAGCCG | | 756 |

( 2 ) INFORMATION FOR SEQ ID NO: 2:

( i ) SEQUENCE CHARACTERISTICS:
        ( A ) LENGTH: 162 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 2:

| | | | | | | | | | | | | | | | |
|---|---|---|---|---|---|---|---|---|---|---|---|---|---|---|---|
| Met | Asn | Ile | Phe | Glu | Asp | Ile | Gly | Asp | Tyr | Val | Pro | Ser | Thr | Thr | Lys |
| 1 | | | | 5 | | | | | 10 | | | | | 15 | |
| Thr | Pro | Arg | Asp | Lys | Glu | Arg | Glu | Arg | Tyr | Arg | Glu | Arg | Glu | Arg | Asp |
| | | | 20 | | | | | 25 | | | | | 30 | | |
| Arg | Glu | Arg | Asp | Arg | Asp | Arg | Asp | Arg | Glu | Arg | Glu | Arg | Glu | Arg | Asp |
| | | 35 | | | | | 40 | | | | | 45 | | | |
| Arg | Glu | Arg | Glu | Arg | Glu | Arg | Asp | Arg | Glu | Arg | Glu | Glu | Glu | Lys | Lys |
| | 50 | | | | | 55 | | | | | 60 | | | | |
| Arg | His | Ser | Tyr | Phe | Glu | Lys | Pro | Lys | Val | Asp | Asp | Glu | Pro | Met | Asp |
| 65 | | | | | 70 | | | | | 75 | | | | | 80 |
| Val | Asp | Lys | Gly | Pro | Gly | Ser | Thr | Lys | Glu | Leu | Ile | Lys | Ser | Ile | Asn |
| | | | | 85 | | | | | 90 | | | | | 95 | |
| Glu | Lys | Phe | Ala | Gly | Ser | Ala | Gly | Trp | Glu | Gly | Thr | Glu | Ser | Leu | Lys |
| | | | 100 | | | | | 105 | | | | | 110 | | |
| Lys | Pro | Glu | Asp | Lys | Lys | Gln | Leu | Gly | Asp | Phe | Phe | Gly | Met | Ser | Asn |
| | | 115 | | | | | 120 | | | | | 125 | | | |

| | | | | | | | | | | | | | | |
|---|---|---|---|---|---|---|---|---|---|---|---|---|---|---|
| Ser | Tyr 130 | Ala | Glu | Cys | Tyr | Pro 135 | Ala | Thr | Met | Asp 140 | Asp | Met | Ala | Val | Asp |
| Ser 145 | Asp | Glu | Glu | Val | Asp 150 | Tyr | Ser | Lys | Met | Asp 155 | Gln | Gly | Asn | Lys | Lys 160 |
| Gly | Pro | | | | | | | | | | | | | | |

RECOMBINANT PRODUCTION OF A HUMAN INTERFERON (IFN)-GAMMA ANTAGONIST CYTOKINE

The present invention relates to a new cytokine which is a specific antagonist of induction by interferon-gamma (IFN-γ) of the expression of class II histocompatibility antigens at the cell surface.

All the cells in the body express glycoproteins known as class I histocompatibility antigens at their surface.

There is also a category of glycoproteins expressed only by immunocompetent cells, the class II histocompatibility antigens. These antigens are encoded by a family of genes located in man on chromosome 6, and which is known as the major histocompatibility complex (MHC), or (HLA) in man.

Class II histocompatibility antigens play an important part during the immune response, especially in the context of interactions between B and T cells or between antigen presenting cells and T cells. Interferon-gamma promotes the functions of immunocompetent cells by inducing the expression of antigens of the major histocompatibility complex (MHC) by numerous cell types (Becker, 1985). The capacity to present the antigen is proportional to the amount of (HLA) class II molecules present on the surface of the accessory cells. Interferon-gamma hence enables these cells to express enough (HLA) class II molecules to present the antigen. The mechanism of interferon-gamma-dependent regulation has not yet been elucidated.

Class II (HLA) antigens are also considered to be differentiation markers: this has been demonstrated for the cells of myeloid lines (Radka et al., 1986) or of fetal liver (Natali et al., 1984), but their function during cell differentiation is not yet established. In addition, the presence of class II antigens might play a part during the phenomenon of tumorigenesis (Festenstein and Garrido, 1986).

The expression of class II antigens is constitutive on B cells. Accolla et al. (1985) and De Préval et al. (1985) have shown that this expression is under the control of a factor which acts in trans at gene level.

A model of regulation of the class II antigens has been proposed by Boss and Strominger (1986). In this model, there are at genomic level, in the 5' flanking region of the gene, 4 successive regions controlling the expression of the histocompatibility antigens: a negative regulatory element, 2 positive control regions and another negative control region. More recent work on the regulation of HLA class II antigens at genomic level has led to the demonstration of a promoter, known as E, in the 5' region of the genes of the major histocompatibility complex, and 2 proteins capable of binding to the Eα promoter (Dorn et al., 1988; Dorn et al., 1989; Koch et al., 1989).

The efficacy of induction differs according to the cell system in question. In effect, some cell lines (K562 leukemic line, embryonic fibroblasts, etc.) are inducible only with difficulty, if at all, whereas other lines (adult fibroblasts, colon carcinoma cells, etc.) express HLA class II antigens after induction by low doses of interferon-gamma.

It was shown in the context of the present invention that the difficulty in obtaining induction of HLA class II antigens by interferon-gamma on so-called refractory cells was due to the spontaneous production of a soluble endogenous inhibitor.

Thus, the present invention relates to a cytokine which is a specific antagonist of induction by interferon-gamma of the expression of class II histocompatibility antigens at the cell surface, and which contains all or part of the peptide sequence as described in FIG. 1*a* (SEQ ID NO:2), as well as the variants that retain the biological activity described above, and is naturally secreted by cells, or is the expression product of an exogenous DNA sequence in prokaryotic or eukaryotic cells.

Although the preferred compound according to the present invention corresponds to the formula in FIG. 1*a*, the present invention also relates to the variants of this cytokine, in particular the variants obtained by deletion, in particular, of the N- or C-terminal ends, the variants obtained by substitution of one or more amino acids and the addition variants obtained by adding one or more amino acid(s), for example the amino acid methionine, at the N-terminal end when the cytokine is expressed in a bacterium.

The present invention also relates to the compounds containing the active epitopes of the cytokine, linked or otherwise to one another via different sequences, and which are also designated variants hereinafter.

Depending on the nature of the host cells used, the cytokine may be glycosylated, so as to be able to undergo the post-translational modifications which are favorable to its biological activity in mammalian cells, or unglycosylated.

The natural protein possesses, besides the features described above, a molecular weight of the order of 19,000 on SDS-polyacrylamide gel, and its inhibitory activity is heat- and trypsin-sensitive.

The protein is precipitable in 50% ammonium sulfate solution.

The protein may be obtained naturally, as a secretion product in the cell culture supernatant. It can also result from the expression of an exogenous DNA sequence in prokaryotic or, more advantageously, eukaryotic cells. In this case, the exogenous DNA sequence can be, in particular, a complementary DNA sequence or alternatively a genomic DNA sequence.

The DNA sequences according to the invention comprise the sequences which enable the new cytokines to be expressed in prokaryotic and eukaryotic host cells.

The sequences according to the invention relate, more specifically, to those chosen from:

a) the DNA sequence of FIG. 1*a* (SEQ ID NO: 1) or its complementary strands;

b) a DNA sequence which hybridizes with the DNA sequences of a) or a portion of these latter; and c) a sequence which, on account of the degeneracy of the genetic code, codes for a cytokine having the same amino acid sequence as a) or b).

d) a sequence which codes for a variant of said cytokine and which retains the biological activity described above.

Thus, the present invention also relates to DNA sequences coding for the expression of variants as are described above. The invention also relates to the DNA sequences that hybridize with the DNA sequences described above, or with one or more fragments thereof.

The sequences according to the invention may be combined covalently or otherwise with a molecule which is labeled, in particular by an isotopic labeling ($^{125}$I, and the like) or by a nonisotopic labeling (biotin, and the like), so that they can be readily detected.

The present invention also relates to eukaryotic or prokaryotic host cells which have undergone a transformation or a transfection with a DNA sequence as described above, so as to effect the expression of said cytokine in the host cell.

The invention also relates to a biologically functional cloning vector comprising a DNA sequence as described above, as well as to eukaryotic or prokaryotic host cells stably transformed or transfected by such a cloning vector.

Biologically functional cloning vector is understood to denote any vector capable of enabling the sequence in question to be expressed in the transformed or transfected host, or alternatively capable of permitting the chromosomal integration of said sequence and its expression under the control of a homologous or heterologous promoter. This type of vector is known in the recombinant DNA field. It can be a plasmid, self-replicating or otherwise, containing an origin of replication which is effective in the host, for example the origin of replication of pBR322 for *E. coli*, as well as the elements providing for the expression of the sequence:

promoter, ribosome binding site, terminator where appropriate, for yeasts for example, as well as various control elements.

These plasmids can also contain marker genes providing for selection in particular, or integration sequences containing homologous sequences providing for integration by recombination.

The vectors in question can also be recombinant viruses, for example vector viruses of the vaccinia type. The methods of transformation and transfection are known and must be suited to the host. The host cells can also have been modified by means of vectors so as to excrete the protein in mature form and/or in fused form.

The present invention also relates to a method for preparing the new protein, characterized in that said cytokine is purified from the cell culture supernatant, or prokaryotic or eukaryotic host cells described above are made to express the cytokine and the desired cytokine is then isolated.

In the case where the cytokine is secreted naturally by cells in culture, the cells are preferably cultured in a suitable nutrient medium lacking the contaminant proteins of serum, the latter being contained in a dialysis bag which is permeable to molecular weights below 50 kD.

This method is also usable when the host cell is a cell which has been treated with a vector as described above and culturing of which necessitates the use of serum, although it is preferable to use hosts which grow on a simple medium.

Cells capable of producing a cytokine according to the invention are fairly numerous; among these, the K562 line available from the National Institute of General Medical Sciences under No. GMO5372D should be mentioned. But it is possible to use other cells, in particular carcinomas or hepatoma cells.

When the cytokines according to the present invention are prepared by the recombinant DNA technique, cells lines such as K562 and its subclones no longer expressing said cytokines are especially advantageous as host cells.

The invention also relates to the antibodies, especially monoclonal antibodies, directed against the cytokines according to the invention. These antibodies can be, in particular, used in the context of a diagnosis of presence of said proteins.

The invention also relates to an immune serum directed against the cytokines described above.

The cytokines according to the present invention may be used as active principle in a therapeutic composition, in the case where it is desired to increase the antagonist effect of these proteins with respect to interferon-gamma.

These therapeutic compositions are usable, most especially, in all states necessitating a modulation of interferon-gamma activity. In particular, the compositions according to the present invention are usable in the treatment and/or prevention of some types of auto-immune diseases, but also in some surgical procedures such as some transplantations.

The compositions according to the invention may also contain other monokines and/or cytokines.

The invention also relates to a therapeutic composition containing as active principle an antibody or an immune serum directed against said cytokine, or even antisense sequences corresponding to the coding sequences, the purpose of which is, in particular, to limit the amounts of cytokine circulating.

The invention also relates to a diagnostic kit enabling the protein to be detected, and containing at least one antibody directed against the latter.

The examples and figures below are designed to bring out further advantages and features of the present invention without, however, limiting its scope. In the figures attached hereto:

FIG. 1*a* shows: the nucleotide sequence of the complementary DNA corresponding to the inhibitor, and the deduced peptide sequence.

(FIG. 2*a*).

EXAMPLE I

DEMONSTRATION OF THE CYTOKINE

1. Cell Culture

K562 cells originating from the pleural effusion of a patient suffering from a chronic myeloid leukemia in blast crisis are cultured in complete RPMI 1640 medium. The cells are placed in an incubator at 37° C. and with 5% $CO_2$. They are inoculated at a concentration of 250,000 cells/ml every 72 h.

ICIG-7 cells, normal human embryonic fibroblast cells (these cells were cultured in our laboratory from normal human embryonic lung), are cultured in a humid incubator at 37° C. and with 5% $CO_2$ in complete MEM medium. Adherent cells which have come to confluence (at 72 h) are detached from their support by the action of trypsin (0.25% in MEM) for 2 to 3 minutes and recultured to a density of 80,000 cells/$cm^2$.

2. Conditioned Medium

K562 cells are cultured under the conditions described above; the culture medium is withdrawn after 72 h, centrifuged, filtered through a 0.22 μm filter and supplemented with 10% FCS and 2 mM glutamine.

3. Interferon-gamma (IFN-gamma)

Unglycosylated recombinant interferon-gamma, produced from *E. coli* bacteria, is obtained from the company Biogen (GENEVA, SWITZERLAND), and its specific activity is $2 \times 10^7$ IU/mg.

Glycosylated recombinant interferon-gamma (DEVOS et al., 1984), produced in hamster CHO cells, possesses a specific activity of $1.3 \times 10^8$ IU/ml.

4. Induction with Interferon-gamma

Cells (K562 or ICIG-7) are cultured in 6-well macroculture plates (9 cm²/well) to a cell density of $5 \times 10^4$ cells/well/2 ml for 72 h in the presence of 1,000 IU/ml of glycosylated recombinant IFN-gamma (CHO) or 10,000 IU/ml of unglycosylated recombinant IFN-gamma (*E. coli*).

5. Test of Biological Activity

ICIG-7 cells are induced under the conditions described in the preceding paragraph, but in the presence of conditioned medium or of the purification fractions which are diluted in complete MEM medium (see purification).

Expression of histocompatibility antigens at the cell surface was determined by the indirect immunofluorescence technique. Cells are washed 3 times in Hanks' medium and then resuspended at a cell density of $5 \times 10^5$ cells/ml. 200 μl of this suspension are distributed in wells of a round-bottomed microplate (96-well). The plate is centrifuged for 5 minutes at 800 g and the supernatant is removed.

The cells are then incubated for 30 minutes at 4° C. in a humid chamber with 20 μl of antibody at a concentration of 10 μg/ml: D1–12 (Carrel et al., 1981) for HLA class II antigens and IOT2 (Immunotech, France) for HLA class I antigens.

After three washes in Hanks' medium by centrifugation for 5 minutes at 800 g and removal of the supernatant, the cells are incubated for 30 minutes at 4° C. in a humid chamber with 20 μl of goat anti-mouse immunoglobulins antibodies coupled to fluorescein (FITC) (Immunotech, France) at the dilution prescribed by the manufacturer. The cells are washed 3 times in Hanks' medium and analyzed by flow cytometry (ATC Odam Brucker France). The analysis is carried out on 5,000 or 10,000 cells at a wavelength of 488 nm. The results are shown in the form of cell distribution histograms, with the fluorescence intensity (logarithmic scale) as abscissae and the number of cells as ordinates.

EXAMPLE II

PURIFICATION OF CYTOKINE

1. Cell Culture

K562 cells are washed 3 times in RPMI 1640 (without phenol red) in order to remove traces of FCS, and then resuspended in RPMI 1640 (without phenol red) with the addition of 2 mM glutamine. A dialysis bag of porosity 50 Kd (Spectrapor 7, Spectrum) containing 10 ml of pure fetal calf serum is introduced into a culture flask containing 90 ml of RPMI 1640 (without either phenol red or FCS) and $2.5 \times 10^7$ cells. For purification, 2 liters of culture were needed.

The cells are cultured for 72 h at 37° C. and the medium is centrifuged at 800 g for 15 minutes; the pellet is removed, and the supernatant is centrifuged again at 800 g for 15 minutes and then filtered through a 0.22 μm filter. PMSF is added to the supernatant at a final concentration of 1 mM.

2. First Purification Step

The supernatant is concentrated 100-fold on an AMICON YM10 membrane and then dialyzed against a large volume of 10 mM/pH 7.4 phosphate buffer containing 1 mM PMSF. An anion exchange column (Mono Q, Pharmacia SWEDEN) is equilibrated with 10 ml of 10 mM/pH 7.4 phosphate buffer. The sample is applied to the column and then eluted by means of 20 ml of an NaCl gradient from 0 to 0.25M in 10 mM/pH 7.4 buffer.

0.5-ml fractions are collected at the column outlet and analyzed on polyacrylamide gel (gradient from 8 to 25%) in the presence of SDS. The gel is then stained with silver nitrate as prescribed by the manufacturer (Phast System, Pharmacia SWEDEN).

The biological activity of each fraction is then tested at several dilutions in complete RPMI 1640 medium according to the protocol described above.

3. Second Purification Step

The fractions containing the biological activity are pooled and concentrated 10-fold on an AMICON YM10 membrane, the sample is applied to a gel filtration column (Superose 12, Pharmacia SWEDEN) and filtration is then performed using a 10 mM phosphate/0.15M NaCl/pH 7.4 buffer. The column had been calibrated beforehand with a set of proteins of known molecular weights (Pharmacia Kit) and equilibrated with 10 mM phosphate/0.15M NaCl/pH 7.4 buffer.

0.25-ml fractions are collected at the column outlet and analyzed according to the protocol described above.

EXAMPLE III

PRODUCTION OF MONOCLONAL ANTIBODIES

1. Immunization

A Balb/C mouse is immunized according to the following protocol:

- a subcutaneous injection of 0.5 ml of a solution containing 10 μg of the purified protein in 0.250 ml of PBS and 0.250 ml of Freund's complete adjuvant.
- 8 days and 21 days later, a second and a third subcutaneous injection of a solution containing 10 μg of the purified protein in 0.5 ml of PBS without Freund's adjuvant.
- a final subcutaneous injection is performed 5 days before cell fusion with a solution containing 10 μg of the purified protein in 0.5 ml of PBS without Freund's adjuvant.

2. Fusion a) on the day before fusion

HAT medium and the fusion solution are prepared.

NS1 mouse myeloma cells are resuspended in complete RPMI 1640 medium at a concentration of 250,000 cells/ml.

Peritoneal macrophages of a Balb/C mouse are removed by washing the peritoneal cavity using 5 ml of cold 0.15M NaCl. The macrophages are centrifuged for 10 minutes at 800 g, then resuspended in HAT medium at a concentration of $5 \times 10^5$ cells/ml and distributed in 5 microculture plates (96-well) on the basis of 100 µl per well. The microplates are then placed in a CO$_2$ incubator (37° C., 7% CO$_2$).

b) on the day of fusion

The NS1 cells are washed 4 times in RPMI 1640 by centrifugation at 800 g for 10 minutes, and the final pellet is then taken up in RPMI 1640 at a concentration of 10$^7$ cells/ml.

The spleen of the immunized mouse is removed and shredded in RPMI 1640, the cells obtained are centrifuged for 10 minutes at 800 g and the pellet is taken up in RPMI 1640 at a concentration of 10$^7$ cells/ml.

Hybridization: cell fusion is carried out by mixing, in a 50-ml tube, 5 ml of spleen cells (5×10$^7$ cells), 3 ml of NS1 cells (3×10$^7$ cells) and 42 ml of RPMI 1640. The tube is centrifuged for 10 minutes at 800 g, and the pellet is taken up in 1 ml of fusion solution, added over 1 minute while constant shaking is maintained. The tube is then immersed for 90 seconds in a water bath at 37° C. while shaking is maintained.

Fusion is stopped by introducing 50 ml of complete RPMI 1640 medium according to the following protocol:

1 ml over 30 seconds 3 ml over 30 seconds 16 ml over 1 minute 30 ml thereafter.

The tube is left for 5 minutes at room temperature and centrifuged for 10 minutes at 200 g, and the pellet obtained is washed twice in complete RPMI 1640 medium by centrifugation for 10 minutes at 200 g. After each centrifugation, the cells are taken up as gently as possible. The cells are resuspended in 50 ml of HAT medium and distributed on the basis of 100 µl/well in microplates containing macrophages. The plates are replaced in the CO$_2$ incubator.

Preservation of clones: the medium is renewed after 6 days of culture by drawing off the supernatant and replacing it with fresh medium. During the second and third weeks of culture, colonies consisting of hybrid cells selected by the medium appear in some wells.

The culture supernatants are sampled to test for the presence of antibodies and the reactivity of the latter; clones of interest are removed and transferred to 24-well macroculture plates containing 2 ml of complete RPMI 1640 medium and 2×10$^6$ spleen cells originating from a normal Balb/C mouse.

It is necessary to subclone in order to check that a secreting clone is maintained during culturing. Subcloning is carried out by limiting dilution; for this purpose, 200 cells are resuspended in 10 ml of complete RPMI 1640 medium and the suspension is distributed in a 96-well microculture plate, and the medium is renewed after 6 days of culture by drawing off the supernatant and replacing it with fresh medium. During the second and third weeks of culture, colonies appear in some wells and the culture supernatants of the clones are tested.

3. Antibody Screening a) ELISA

Binding of the purified protein to microELISA microplates is carried out by incubation for 1 h at 37° C., with 100 µl per well, of a solution of the protein at a concentration of 0.1 µg/ml in a pH 9.6 0.5M carbonate/bicarbonate buffer. The excess proteins are removed by 5 washes in NaCl/Tween buffer. The plate is then saturated for 1 h at 37° C. using a PBS/3% BSA (bovine serum albumin) solution. After 5 washes in NaCl/Tween buffer, 100 µl/well of culture supernatants of the different clones, previously diluted to ½ in PBS/0.1% Tween 20, are added and incubated for 1 h 30 min at 37° C.

After 5 washes in NaCl/Tween buffer, visualization of the mouse immunoglobulins bound to the plate is performed by incubation with 100 µl/well of peroxidase-labeled goat anti-mouse immunoglobulins antibodies diluted (to the dilution prescribed by the manufacturer) in PBS/0.05% Tween 20/3% BSA. The plates are incubated for 1 h 30 min at 37° C. and then washed 5 times in NaCl/Tween buffer.

The content of peroxidase-labeled antibodies bound to the plate is evaluated by determining peroxidase activity using a solution of ortho-phenylenediamine (OPD) in an OPD buffer in the presence of hydrogen peroxide (H$_2$O$_2$) (40 mg of OPD per 100 ml of buffer and 20 µl of 110-volumes H$_2$O$_2$ are added at the time of use).

200 µl of this OPD solution are introduced into each well, the coloration appears after a few minutes in darkness and the reaction is then stopped by adding 50 µl/well of 0.1N H$_2$SO$_4$. The optical density is measured at 492 nm using an automatic spectrophotometer for reading plates.

b) Blocking of inhibitory activity

ICIG-7 cells are cultured in 6-well macroculture plates (9 cm$^2$/well) to a cell density of 5×10$^4$ cells/well/2 ml for 72 h in the presence of 1,000 IU/ml of recombinant IFN-gamma (CHO), the purified protein and hybridoma supernatants diluted to ½, in complete MEM medium containing antibodies.

c) immunoblotting

The supernatant of K562 cells is concentrated 100-fold on an AMICON YM10 membrane and then dialyzed against a large volume of 10 mM/pH 7.4 phosphate buffer. 10 µl of this solution are diluted in 40 µl of Laemmli sample buffer. The sample is brought to 100° C. for 2 minutes and then applied to a polyacrylamide gel with a gradient from 8 to 25% (Pharmacia); after migration and transfer onto a 0.45 µm nitrocellulose membrane (according to the protocol prescribed by the manufacturer, PhastSystem and Phast-Transfer Pharmacia), the membrane is incubated for 30 minutes at room temperature in a PBS/3% BSA solution.

The nitrocellulose is cut into strips to test the reactivity of the different monoclonal antibodies with respect to the molecule. Each strip is incubated overnight at 4° C. with 2 ml of each hybridoma culture supernatant diluted to ½ in a PBS/0.1% Tween 20 solution. After 3 washes of 5 minutes in NaCl/Tween buffer, the strips are incubated for 1 h 30 min at room temperature with rabbit anti-mouse immunoglobulins antibodies (Rabbit anti Mouse, DAKO 2412) diluted to 1/500 in NaCl/Tween buffer.

After 4 washes in NaCl/Tween buffer, the strips are incubated with APAAP Complex (Sera Lab) diluted to 1/400 in NaCl/Tween buffer for 1 h 30 min at room temperature. The strips are washed again 4 times in NaCl/Tween buffer. Bound antibodies are visualized according to the following protocol: 400 µl of NBT (50 mg/ml) are added to 60 ml of NBT buffer and, after dissolution, 200 µl of BCIP (50 mg/ml) are added to the solution. The strips are left in this solution for approximately 5 minutes; then washed with water and dried on a Whatman 3 MM Chr paper.

EXAMPLE IV

CLONING OF A COMPLEMENTARY DNA

1. Screening of an Expression Library in lambda gt11 a) Preparation of Y1090 bacteria

An isolated colony is removed and incubated at 37° C. with agitation for 3 to 4 h in 1 ml of LB, and the bacteria are then transferred to 50 ml of LB and incubated overnight at 37° C. with agitation. The bacteria are centrifuged for 20 minutes at 1,200 g and the pellet is taken up in 20 ml of SM buffer.

b) Titration of the K562 lambda gt11 library (Clontech)

300 µl of Y1090 bacteria are added to 100 µl of phages diluted to 1/500,000 in SM buffer; the phage/bacteria mixture is incubated for 25 minutes at 37° C. 7.5 ml of soft agar (top agar) are added and immediately plated out on a 150 mm dish containing LB/agar/ampicillin. The dish is incubated at 42° C. for 4 h, and the lytic plaques are then counted to determine the titer of the library.

c) First round of screening 6 tubes are prepared for the test: 100 µl of suspension containing $3 \times 10^4$ phages, originating from the library, in SM/10 mM $MgSO_4$ buffer are added to 300 µl of Y1090 bacteria in freshly prepared SM; the mixture is incubated for 25 minutes at 37° C. 7.5 ml of top agar are added to each tube and immediately plated out on a 150 mm dish containing LB/agar/ampicillin. The dishes are incubated at 42° C. for 4 h. 6 0.45 µm nitrocellulose filters are dipped in 10 mM IPTG solution and dried for a few minutes before being laid on the dishes. The dishes are then incubated at 37° C. for 2 h. The filters are removed and then incubated for 30 minutes at laboratory temperature in PBS/3% BSA buffer (the dishes are stored at 4° C. during the remainder of the test).

The filters are transferred to a mixture of 4 antibodies, chosen from those produced, in the form of ascites and diluted to 1/500 in NaCl/Tween buffer. The filters are incubated overnight at 4° C., washed for 4 times 5 minutes in NaCl/Tween buffer and then incubated for 1 h 30 min at laboratory temperature with rabbit anti-mouse immunoglobulins antibodies (Rabbit anti Mouse DAKO Z412) diluted to 1/500 in NaCl/Tween buffer.

After 4 washes of 5 minutes in NaCl/Tween buffer, the filters [lacuna] incubated with APAAP Complex (Sera Lab) diluted to 1/400 in NaCl/Tween buffer for 1 hour 30 min at room temperature. The filters are washed again 4 times in NaCl/Tween buffer. Positive lytic plaques are visualized according to the following protocol: 400 µl of NBT (50 mg/ml) are added to 60 ml of NBT buffer and, after dissolution, 200 µl of BCIP (50 mg/ml) are added to the solution. The filters are left in this solution in darkness until a positive lytic plaque appears (approximately 5 minutes); the filters are then washed with water and dried on a Whatman 3 MM Chr paper for a few minutes.

d) Second round of purification

The lytic plaques which are positive in the first round are removed using an inverted Pasteur pipette, and each plug so removed is left to diffuse overnight in I ml of SM/10 mM $MgSO_4$ buffer. The phages are titrated as described for the titration of the library.

For each lytic plaque, a suspension of 200 phages in 100 µl of SM/10 mM $MgSO_4$ buffer are added to 100 µl of Y1090 bacteria freshly prepared in SM. The mixture is incubated for 25 minutes at 37° C. 3.5 ml of top agar are added to each tube and immediately plated out on a 90 mm dish containing LB/agar/ampicillin. The dishes are incubated at 42° C. and treated as in the first round.

e) Third round of purification

The lytic plaques which are positive in the second round are removed using a Pasteur pipette, and each plug so removed is left to diffuse overnight in 1 ml of SM/10 mM $MgSO_4$ buffer. The phages are titrated as described for the titration of the library. For each lytic plaque, a suspension of 50 phages in 100 µl of SM/10 mM $MgSO_4$ buffer is added to 100 µl of Y1090 bacteria freshly prepared in SM. The mixture is incubated for 25 minutes at 37° C. 3.5 ml of top agar are added to each tube and immediately plated out on a 90 mm dish containing LB/agar/ampicillin. The dishes are incubated at 42° C. and treated as in the first round.

f) Phage amplification on dishes

A suspension of $5 \times 10^4$ phages to be amplified in 100 µl of SM/10 mM $MgSO_4$ buffer is added to 300 µl of Y1090 bacteria freshly prepared in SM, and the mixture is incubated for 25 minutes at 37° C. 7.5 ml of top agar are added to each tube and immediately plated out on a 150 mm dish containing LB/agar/ampicillin. The dishes are incubated at 42° C. for 4 h, and then overnight at 4° C. in 10 ml of SM. The diffusion product is recovered, and the dish rinsed with 5 ml of SM buffer. The phages are titrated as described for the titration of the library.

g) Preparation of purified phages

An isolated colony of Y1090 bacteria is removed and incubated at 37° C. with agitation for 3 to 4 h in 1 ml of LB, then transferred to 50 ml of LB and incubated overnight at 37° C. with agitation. The bacteria are centrifuged for 20 minutes at 1,200 g and the pellet is taken up in 20 ml of SM buffer. The concentration of the bacteria is estimated (one OD unit at 600 mm corresponds to $8 \times 10^8$ bacteria/ml).

The bacteria and the phages are brought into contact at a multiplicity of 20 : $12 \times 10^9$ bacteria in 100 µl of SM/10 mM $MgSO_4$ are incubated for 25 minutes at 37° C., and 400 ml of LB/10 mM $MgSO_4$ are then added to the mixture. The preparation is incubated for 3 to 4 h at 37° C. with agitation. The optical density at 600 nm is measured every hour; it should reach 1.5 and fall back to 0.5. Chloroform is added (2 ml per 400 ml).

The mixture is incubated for 20 minutes at 37° C. with agitation. After centrifugation for 30 minutes at 10,000 RPM at 4° C., the supernatant is recovered, and DNAse and RNAse at a final concentration of 2.5 µg/ml are added.

The preparation is incubated for 45 minutes at 37° C. with agitation, and 24 g of NaCl (per 400 ml) and 40 g of PEG 6000 (per 400 ml) are added successively. After precipitation for 1 h (or overnight) at 0° C., the mixture is centrifuged at 10,000 RPM for 30 minutes at 4° C. The supernatant is removed and the tube is drained onto an absorbent paper. The pellet is taken up in 1 ml of SM buffer, and 10 µl of 10% SDS and 10 µl of pH 8 0.5M EDTA are then added. The tube is incubated for 15 minutes at 68° C.

Successive extractions are performed: 1) chloroform, 2) 2 phenol extractions, 3) 2 phenol/chloroform extractions, 4) chloroform, 5) 4 ether extractions. The final aqueous phase is incubated for 40 minutes at 65° C., then precipitated with 1 volume of cold isopropanol and centrifuged for 15 minutes at 4° C. at 12,000 g. The supernatant is removed and the pellet washed in 500 µl of 80% ethanol and then centrifuged for 15 minutes at 4° C. and at 12,000 g. The pellet is taken up in 50 µk of pH 8 TE buffer and, after measurement of the OD at 260 nm, the concentration adjusted to 100 µg/ml.

h) Purification of the insert from the phage

The insert is recovered after digestion with the restriction enzyme EcoRI:

25 µl of purified phages (2.5 µg)

50 µl of 10× enzyme buffer (supplied by the manufacturer)

415 µl of MilliQ (Millipore) distilled water

10 µl of EcoRI enzyme (9 IU/µl)

The mixture is incubated for 1 h 30 min at 37° C., and then for 30 minutes at 37° C. after the addition of 10 µl of RNAse (10 µg/ml). (The RNAsc is brought to 100° C. for 20 minutes and then cooled in ice before use).

Digestion is monitored on 1% agarose gel in 1× TAE buffer; for this purpose, 8 µl of the solution are sampled and 2 µl of loading buffer are added. Migration takes place at 80 volts in a mini-electrophoresis cell in the presence of 1× TAE buffer and BET at a concentration of 0.5 µg/ml.

500 µl of the digestion solution are transferred to an Eppendorf tube and 500 µl of V/V phenol/chloroform are added. After shaking of the tube and centrifugation for 5 minutes at 12,000 g, the upper aqueous phase is transferred to 2 fresh tubes for precipitation. 250 µl of 4M ammonium acetate and 1 ml of cold absolute ethanol are added. The tubes are left for 15 minutes in dry ice, warmed for a few seconds and centrifuged for 15 minutes at 12,000 g at 4° C.

The supernatant is carefully removed and the pellet washed in 500 µl of 80% ethanol, centrifuged for 15 minutes at 12,000 g at 4° C. and then dried. The pellet is taken up in 10 µl of distilled water.

2. Subcloning of the Purified Insert in Plasmid pBLSCR a) Preparation of plasmid pBLSCR KS (Stratagene)

The plasmid is digested with EcoRI:

20 µl of plasmid (1 µg/µl)

10 µl of 10× enzyme buffer (supplied by the manufacturer)

60 µl of distilled water

10 µl of EcoRI (9 IU/µl)

The mixture is incubated for 1 h at 37° C., and digestion is verified on 1% agarose gel as described above.

100 µl of the digestion solution are transferred to an Eppendorf tube and 100 µl of V/V phenol/chloroform are added. After shaking of the tube and centrifugation for 5 minutes at 12,000 g and at 4° C., the upper aqueous phase is transferred to a fresh tube. 100 µl of 4M ammonium acetate and 500 µl of cold absolute ethanol are added, and the tube is left for 15 minutes in dry ice, warmed for a few seconds and centrifuged for 15 minutes at 12,000 g at 4° C.

The supernatant is carefully removed and the pellet washed in 500 µl of 80% ethanol, centrifuged for 15 minutes at 12,000 g at 4° C. and then dried. The pellet is taken up in 10 µl of distilled water. The plasmid is treated with phosphatase:

10 µl of plasmid

10 µl of 10× buffer

5 µl of phosphatase (1 IU)

75 µl of distilled water

The tube is incubated for 1 h 30 min at 37° C., the plasmid is then precipitated as described above and the pellet is taken up in 10 µl of pH 8 TE buffer.

b) Purification of the plasmid and the insert on gel

A 0.8% gel of SeaPlaque GTG agarose (FMC BioProducts) is prepared in 1× TAE buffer. 2 µl of loading buffer are added, either to 10 µl of plasmid, or to 10 µl of phage DNA. The samples are applied to the gel and migration takes place at 20 volts in 1× TAE buffer in the presence of BET at a final concentration of 0.5 µg/ml; until the migration front reaches 10 cm.

The strips of agarose corresponding to the plasmid and to the insert are cut out under UV and recovered in Eppendorf tubes, the tubes are heated to 65° C. and the volume of molten agarose is measured.

c) Ligation

For ligation, a tube containing:

2 µl of purified vector (200 ng),

2 µl of purified insert (200 ng),

2 µl of 10× ligase buffer (supplied by the manufacturer),

12 µl of distilled water, and 2 µl of T4 DNA ligase is incubated overnight at 15° C. A tube is also prepared omitting the insert.

d) Calcium transformation

1) Preparation of competent bacteria

An isolated colony of HB101 bacteria is removed and placed uncultured in 50 ml of LB with agitation at 37° C. overnight. The density is measured at 600 nm and the bacteria are diluted in LB to obtain 500 ml of bacteria having an optical density of 0.1. The bacteria are recultured at 37° C. with agitation until an optical density of 0.6 is obtained; then cooled as quickly as possible to 0° C. and centrifuged at 0° C. at 1,500 g for 5 minutes; the supernatant is removed and the pellet taken up in 500 ml of cold 50 mM $CaCl_2$ and incubated for 1 h at 0° C. After centrifugation for 5 minutes at 1,200 g at 0° C., the supernatant is removed and the bacteria are resuspended in 50 ml of 50 mM $CaCl_2$/20% glycerol. The bacteria are either used immediately, or frozen at −80° C. in aliquots.

2) Transformation

In a sterile 5-ml tube, for each ligation, kept in ice:

20 µl pH 8 10 mM Tris-HCl

5 µl of the ligation product

10 µl of 10× TMC buffer

65 µl of competent bacteria (freshly prepared or frozen).

The tubes are incubated for 15 minutes at 4° C., then 2 minutes at 42° C. and lastly 10 minutes at room temperature. 1 ml of LB is added to each tube and the latter are incubated for 1 h at 37° C., and 300 µl of this suspension are plated out on a 90 mm dish containing LB/agar/ampicillin. The dishes are incubated overnight at 37° C.

e) Plasmid Minipreparation

Colonies are removed from the dishes using toothpicks, placed in tubes containing 3 ml of LB and then incubated overnight at 37° C. with agitation. 1.2 ml of each suspension are transferred to Eppendorf tubes and the bacteria are recovered by centrifugation for 15 minutes at 12,000 g (4° C.).

The supernatant is removed and the pellet taken up in 100 µl of TELT buffer and 10 µl of lysozyme. The tubes are placed for 1 minute at 100° C. and 5 minutes in ice, and then centrifuged for 10 minutes at room temperature. The pellet is removed using a toothpick, 220 µl/tube of cold absolute ethanol are then added and the tubes are placed in dry ice for 15 minutes. The tubes are warmed and then centrifuged for 15 minutes at 4° C. and at 1,200 g, the supernatants removed and the pellets washed with 500 µl/tube of cold 80% ethanol and centrifuged for 10 minutes at 12,000 g at 4° C. The pellets are dried, and each pellet is then taken up in 30 µl of pH 7.5 10 mM Tris-HCl.

f) Verification of the presence of the insert

10 µl of minipreparation

2 µl of EcoRI enzyme buffer

6 µof distilled water

2 µl of EcoRI 50 IU/µl.

The tubes are incubated for 1 h at 37° C. 10 µl of each preparation, digested or otherwise, are applied to agarose gel, 1% of 1× TAE buffer, and migration takes place at 80 volts in 1× TAE buffer containing BET at a final concentration of 0.5 µg/ml.

3. Sequencing of the cDNA Obtained a) Plasmid amplification and purification

One of the plasmids containing the insert is amplified; for this purpose, 50 µl of bacteria containing the plasmid of interest are incubated overnight at 37° C. and with agitation in 10 ml of LB containing ampicillin.

The optical density is measured at 600 nm, and the bacteria are diluted in LB containing ampicillin to obtain 500 ml of culture having an optical density of 0.1. The bacteria are incubated overnight at 37° C. and with agitation in a 2-liter Erlenmeyer. The bacteria are centrifuged for 20 minutes at 4° C. and at 12,000 g, and purification of the plasmid is performed according to the manufacturer's directions on a Quiagen column.

b) Oligonucleotide synthesis

Oligonucleotide synthesis is carried out using an automatic synthesizer (Applied Biosystem); the oligonucleotide obtained is bound to a column. It is eluted from this column by 3 passages of 25% ammonia solution (300 µl, 300 µl and 400 µl) using a 1 ml syringe and recovered at the other end using another syringe. Each introduction of ammonia solution is accompanied by a 15-minute incubation at room temperature. The oligonucleotide is recovered in a tube which is placed at 65° C. overnight.

The oligonucleotide is precipitated in 1 volume of 4M ammonium sulfate and two and a half volumes of cold absolute ethanol, and the tube is placed in dry ice for 15 minutes, warmed and centrifuged for 15 minutes at 12,000 g at 4° C. The supernatant [lacuna] removed and the pellet washed in 500 µl of cold 80% ethanol. The pellet is dried and taken up in 500 µl of distilled water. Measurement of the optical density is carried out at 260 nm, and the oligonucleotide concentration is adjusted to 0.8 µM, which is usable for sequencing.

c) Sequencing

Sequencing was carried out using the Pharmacia T7 sequencing kit, according to the technique described by the manufacturer. The product of the reaction undergoes electrophoresis on 8% polyacrylamide gel 0.4 mm in thickness in the presence of 46% urea and in 1× TBE buffer. Two applications of each sequencing reaction are carried out at an interval of 2 h.

The sequence was determined by several reactions. The first two sequencing reactions were carried out using two oligonucleotides corresponding to the insertion site of the insert in the plasmid. The next two sequencing reactions were carried out using 2 15-mer oligonucleotides corresponding to the last bases capable of being read on the insert. The next sequencing reactions were carried out in the same manner, that is to say 2 new oligonucleotides were chosen and synthesized. Successive reactions were carried out until the complete sequence was obtained.

4. Amplification of the phage insert by PCR

Amplification of the insert by PCR was carried out on a Perkin Elmer Cetus apparatus.

From the stock solution containing $3 \times 10^7$ phages/ml, 10 µl are sampled and 40 µof distilled water added. The sample is brought to 100° C. for 2 minutes and centrifuged at 12,000 g for 10 minutes; the supernatant is recovered (= DNA for PCR).

PCR reaction:

10 µl DNA for PCR

10 µl of 10× enzyme buffer

2 µl of 124 µM dNTPs

1 µl Oligonucleotides 1 (50 pM)

1 µl Oligonucleotides 2 (50 pM)

1 µl Oligonucleotides 1 (or 2) labeled with [$^{32}$P]ATP (3 pM)

0.5 µl of Taq enzyme (0.5 IU/µl)

75.5 µl of distilled water.

30 cycles:

Denaturation: 30 seconds at 94° C.

Oligonucleotide binding: 40 seconds at 55° C.

Extension: 40 seconds at 72° C.

The extension of the final cycle lasts 10 minutes.

5. Sequencing after PCR

The PCR product is used for sequencing according to the Maxan and Gilbert technique on pieces of paper (for Maxam and Gilbert sequencing, Amersham RPN 1500).

A+G reaction: the paper is incubated for 10 minutes at room temperature in 1 ml of 66% aqueous formic acid.

C reaction: the paper is incubated for 10 minutes at room temperature in 1 ml of pH 6 hydroxylamine/hydrochloride 275 mg/ml.

G reaction: the paper is incubated for 5 minutes at room temperature in 1 ml of pH 3.5 50 mM ammonium formate containing 7 µl of DMS.

T+C reaction: the paper is incubated for twice 10 minutes at room temperature in twice 1 ml of potassium permanganate 2 mg/ml.

Each fragment is washed for 3 times 30 seconds in distilled water and one times 30 seconds in 96% ethanol; the paper is dried in the air for 2 minutes between each wash. The fragments are then transferred to Eppendorf tubes containing 300 µl of piperidine; after 30 minutes at 90° C., the fragments are removed and the tubes are placed to dry.

The pellets are taken up in 40 µof distilled water per tube and then dried. This operation is repeated 3 times. Each pellet is taken up in 15 µl of loading buffer for stopping the sequencing (Pharmacia kit), and the samples are applied to an 8% polyacrylamide gel as described above.

6. Subcloning of the purified insert in the vector CDM8

The insert purified from the phage is treated with Klenow enzyme:

20 µl of insert (200 ng)

2 µl of dATP (0.5 mM)

2 µl of dCTP (0.5 mM)

2 µl of dGTP (0.5 mM)

2 µl of dTTP (0.5 mM)

4 µl of 10× enzyme buffer

6 µl of distilled water

2 µl of Klenow enzyme (2 IU/µl)

The tube is incubated for 30 minutes at 37° C., and the DNA is then precipitated by adding one volume of 4M ammonium acetate and 2.5 volumes of cold absolute ethanol; the tube is placed for 15 minutes in dry ice, warmed and centrifuged at 12,000 g for 15 minutes at 4° C. After removal of the supernatant, the pellet is washed in 500 µl of cold 80% ethanol, centrifuged for 15 minutes at 12,000 g at 4° C., dried and taken up in 10 µl of distilled water.

Ligation:

5 µl of this solution

3 µl of BstX1 adaptors (3 µg)

1 µl of 10× enzyme buffer

1 µl of T4 DNA ligase (2.5 IU/µl).

The tube is incubated at 15° C. overnight, and the unbound adaptors are removed on a column of Pharmacia Sephadex S400 according to the protocol described by the manufacturer. The recovered DNA is precipitated as described above and the pellet is taken up in 21 µl of distilled water.

Then 4 µl of vector CDM8 cut with BstX1 (In vitrogen 0.2 µg/µl), 3 µl of ligation buffer (supplied by the manufacturer)

and 2 μl of T4 DNA ligase (2.5 IU/μl) are added, and the tube is incubated at 15° C. overnight. The tube can be stored at −20° C.

7. Verification of the Direction of Insertion of the Insert a) Preparation of competent bacteria An isolated colony of bacteria is removed and cultured in 50 ml of LB with agitation at 37° C. overnight. The density is measured at 600 nm, and the culture is diluted in LB to obtain 500 ml of bacteria having an optical density of 0.1. The bacteria are recultured at 37° C. with agitation until an optical density of 0.4 to 0.5 at 600 nm is obtained; the bacteria are cooled as fast as possible to 0° C. and left for 15 minutes at 0° C.

The bacteria are centrifuged at 0° C. at 1,200 g for 20 minutes, the supernatant is removed and the pellet is taken up in ½ initial volume of cold distilled water; the operation is repeated 4 times. The supernatant is removed and the pellet is taken up in 1 volume of 30% glycerol; the bacteria are either used immediately, or frozen at −80° C. in aliquots.

b) Electroporation

2 μl of the ligation product and 50 μl of competent bacteria are mixed in a 0.2 cm electroporation cell, and the apparatus is set to 2,470 mV, 400 ohms, 25 μF.

Immediately after electroporation, the bacteria are taken up in 1 ml of SOC medium and then incubated for 1 h with agitation at 37° C. The bacteria are plated out on the basis of 10 μl, 100 μl or 500 μl on 3 dishes of LB/agar/ampicillin/tetracycline. The dishes are incubated overnight at 37° C. Minipreparations are made in order to verify the insertion, as described above.

From colonies possessing the insert, larger preparations of plasmids are made as described above. Sequencing is then performed to determine the direction of insertion.

8. Transformation of COS cells

One of the plasmids, having the direction of insertion permitting synthesis of the protein, is used for the electrophoresis of COS cells.

COS cells are inoculated in complete DMEM medium and are collected after 24 h (50 to 70% confluence). The cells are washed twice in cold PBS by centrifugation at 800 g for 5 minutes and resuspended at $10^7$ cells/ml in electroporation buffer.

0.8 ml of cell suspension and 60 μg of plasmid/insert are mixed in a 0.4 cm electroporation cell. The cell is placed in ice for 10 minutes, and the apparatus is set to 380 mV, 25 μF. Immediately after electroporation, the cell is placed in ice for 10 minutes and the cells are then recultured in a 75-cm$^2$ flask. The supernatant is removed 48 hours later for testing.

9. Verification of the Activity of the Recombinant Protein

The supernatant of the electroporated COS cells is used in a test of induction of ICIG-7 cells, the supernatant is used at different dilutions in complete MEM medium and the test is carried out as described above.

REFERENCES

ACCOLLA R. S., CARRA G., GUARDIOLA J.; P. N. A. S., 1985, 82: 5145–5149.
BECKER S.; Surv. Immunol. Res., 1985, 4: 134–145.
BOSS J. M., STROMINGER J. L.; P. N. A. S., 1986, 83: 9139–9143.
DE PREVAL C., LISOWSKA-GROSPIERRE B., LOCHE M., GRISCELLI C., MACH B.; Nature, 1985, 318: 291–293.
DORN A., FEHLING H. J., KOCH W., LE MEUR M., GERLINGER P., BENOIST C., MATHIS D.; Molecular and Cellular Biology, 1988, 8: 3875–3987.
DORN A., BENOIST C., MATHIS D.; Molecular and Cellular Biology, 1989, 9: 312–320.
FESTENSTEIN F., GARRIDO G.; Nature, 1986, 322-502-503.
KOCH W., BENOIST C., MATHIS D.; Molecular and Cellular Biology, 1989, 9: 303–311.
NATALI P. G., SEGATTO O., FERRONE S., TOSI R., CORTE G.; Immunogenetics, 1984, 19: 109–116.
RADKA S. F., CHARRON D. J., BRODSKY F. M.; Hum. Immunol., 1986, 16: 390–400.

We claim:

1. An isolated nucleic acid molecule comprising a nucleotide sequence selected from the group consisting of:
   (a) a sequence which encodes a polypeptide comprising the amino acid sequence shown in SEQ ID NO: 2;
   (b) a sequence which encodes a polypeptide comprising an amino acid sequence which differs from that shown in SEQ ID NO: 2 by the substitution of one amino acid, wherein said polypeptide is capable of specifically antagonizing the induction by IFN-γ of the expression of class II histocompatibility antigens at the surface of a human cell; and
   (c) a sequence complementary to the full length of the sequence of (a) or (b).

2. A nucleic acid molecule according to claim 1, wherein said nucleic acid encodes the cytokine having the amino acid sequence shown in SEQ ID NO: 2.

3. A nucleic acid molecule according to claim 1, wherein said nucleic acid is a DNA molecule comprising the coding sequence shown in SEQ ID NO: 1.

4. A nucleic acid molecule according to claim 1, wherein said nucleic acid is complementary to the full length of the coding sequence shown in SEQ ID NO: 1.

5. A nucleic acid molecule according to any one of claims 1 to 4, wherein the nucleic acid is detectably labeled.

6. A labeled nucleic acid according to claim 5, wherein the label is a radioisotope.

7. A labeled nucleic acid according to claim 5, wherein the label is other than a radioisotope.

8. A vector comprising a nucleic acid according to any one of claims 1 to 4.

9. A host cell transformed or transfected with a nucleic acid according to any one of claims 1 to 4.

10. A host cell according to claim 9, prepared by a process comprising the step of introducing said nucleic acid into said cell in a vector.

11. A host cell according to claim 9, wherein said cell is a eukaryotic cell.

12. A method for preparing a cytokine polypeptide, comprising the steps of
    providing a transformed or transfected host cell according to claim 9, wherein said nucleic acid encodes a polypeptide comprising the amino acid sequence shown in SEQ ID NO: 2 or a polypeptide which differs from SEQ ID NO: 2 by the substitution of one amino acid;
    culturing said host cell under conditions suitable for the expression of said nucleic acid; and
    purifying said cytokine from the cell culture.

13. A method according to claim 12, wherein said culturing is performed in a serum-free medium.

* * * * *

UNITED STATES PATENT AND TRADEMARK OFFICE
CERTIFICATE OF CORRECTION

PATENT NO. : 5,612,195
DATED : March 18, 1997
INVENTOR(S) : Krief et al.

It is certified that error appears in the above-identified patent and that said Letters Patent is hereby corrected as shown below:

On the title page, item [22] PCT Filed, please delete " Feb. 12, 1992 " and insert -- Dec. 2, 1992 --.

In column 4 at line 2, please delete " - ".

Figure 1B:
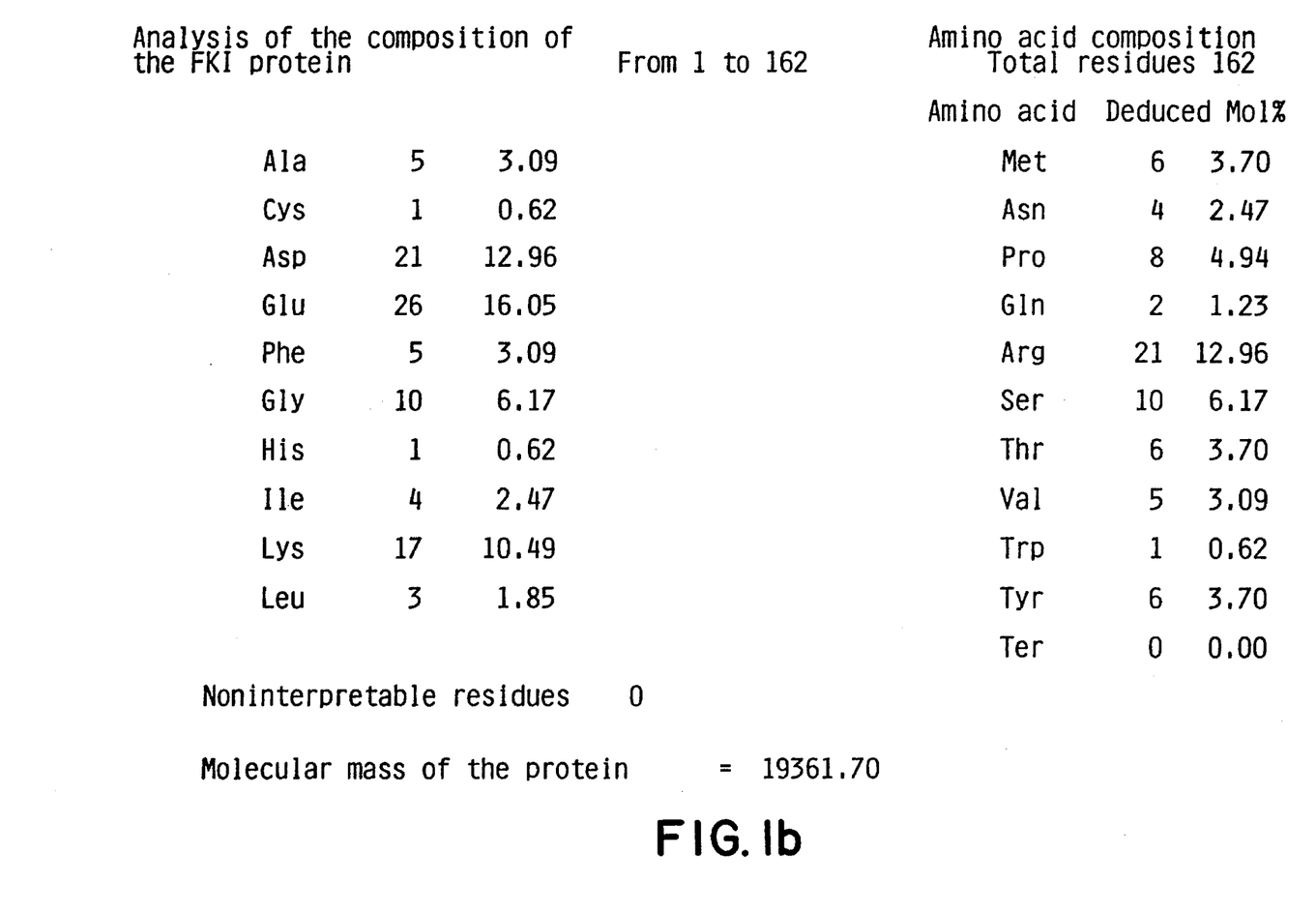
FIG. 1*b* presents a summary of the sequence composition of the inhibitor.
Figure 2A:
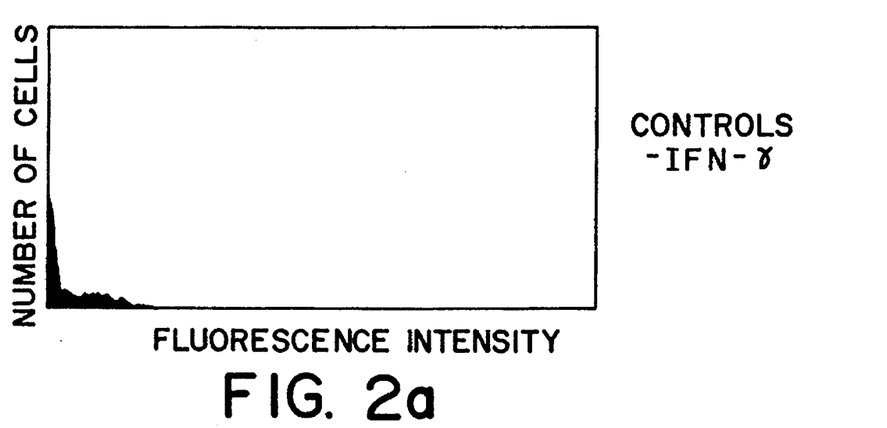
FIG. 2*a*–2*c* show the histograms obtained on a flow cytometer (E. C. Coulter) for expression of HLA DR (FIG. 2*b*) and HLA class I (FIG. 2*c*) antigens on K562 cells after induction with glycosylated interferon-gamma at a concentration of 1,000 IU/ml. Also shown are, negative controls without interferon-gamma, with or without the specific antibodies (the curves are coincident).
Figure 2B:
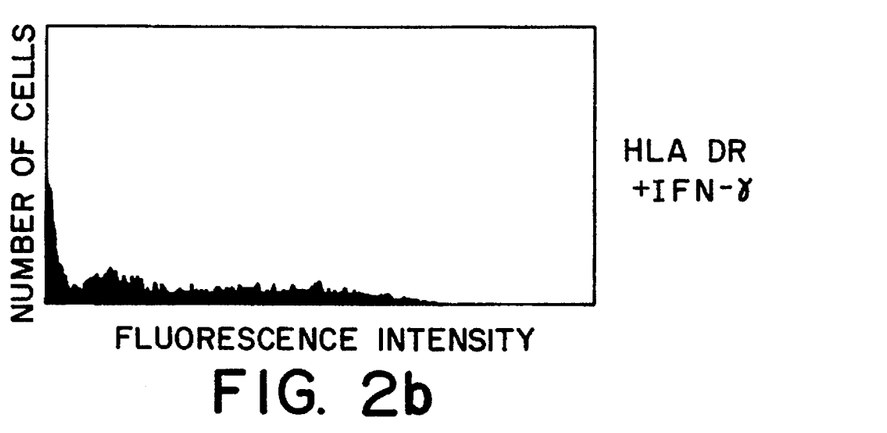
Figure 2C:
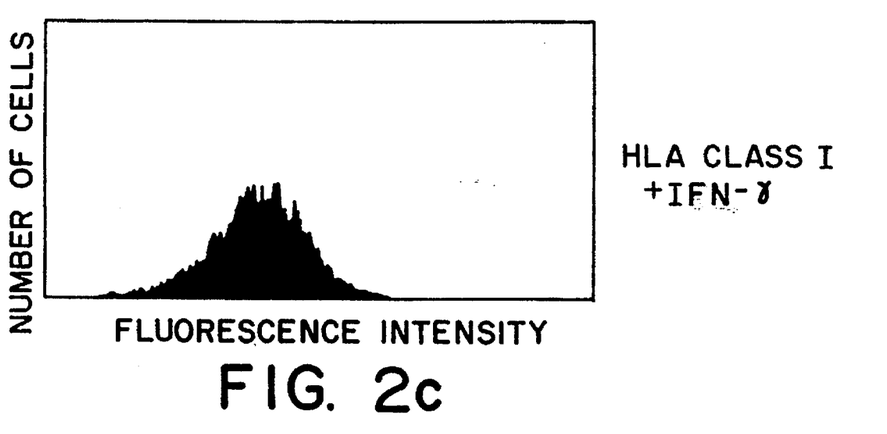
Figure 2D:
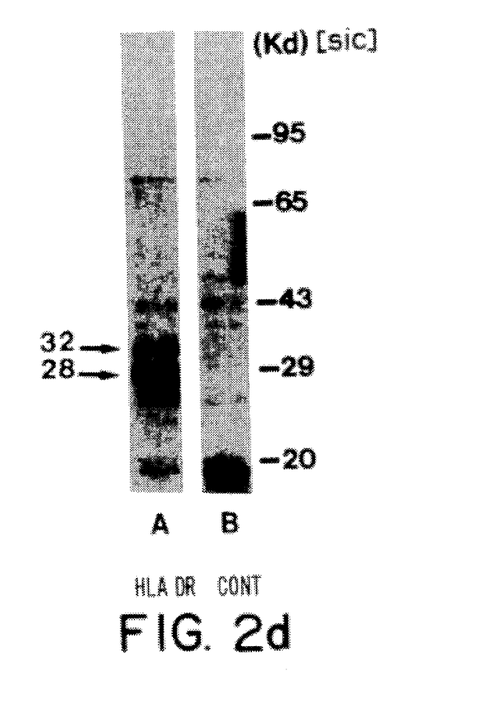
FIG. 2*d* shows the immunoprecipitation of the alpha (32 kD) and beta (28 kD) chains of the HLA DR antigens induced by interferon-gamma on K562 cells (A), negative control (B).
Figure 3A:
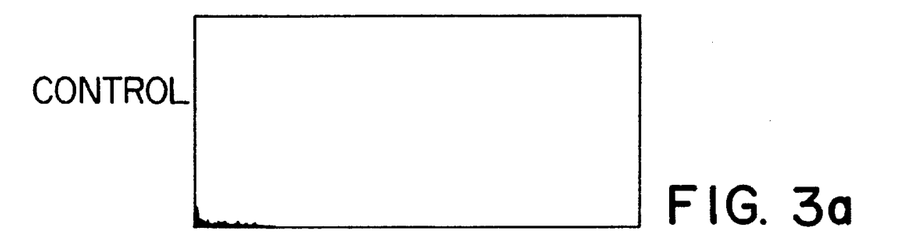
FIG. 3*a–e* shows: the histograms obtained on a flow cytometer (E. C. Coulter) for expression of HLA DR (FIG. 3*b*) and HLA class I (FIG. 3*d*) antigens on ICIG-7 cells after induction with glycosylated interferon-gamma at a concentration of 100 IU/ml. At (FIG. 3*a*), negative controls without interferon-gamma, with or without the specific antibodies (the curves are coincident). Expression of the HLA DR (FIG. 3*c*) and HLA class I (FIG. 3*e*) antigens on ICIG-7 cells after induction with glycosylated interferon-gamma at a concentration of 100 IU/ml and in the presence of conditioned medium from K562 cells.
Figure 3B:
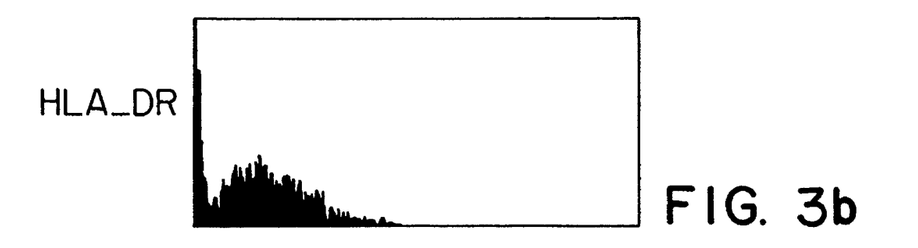
Figure 3C:
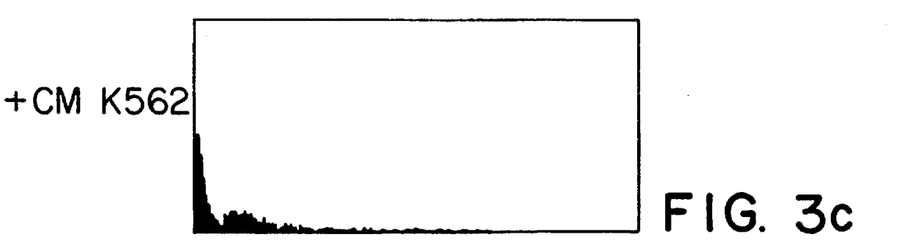
Figure 3D:
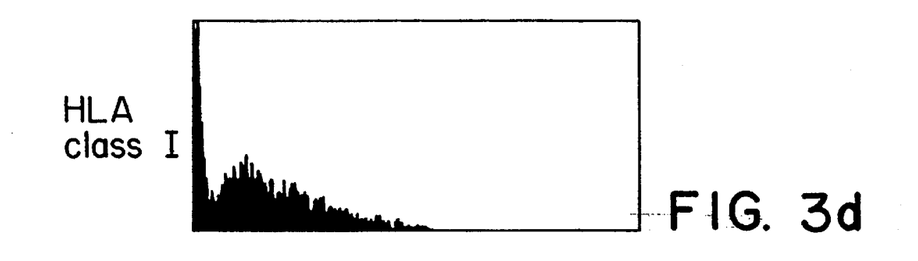
Figure 3E:
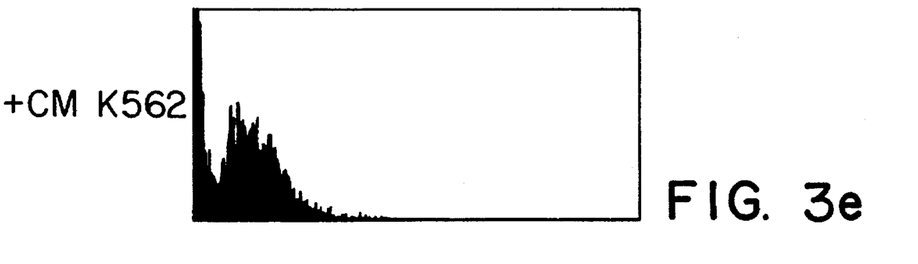
Figure 4A:
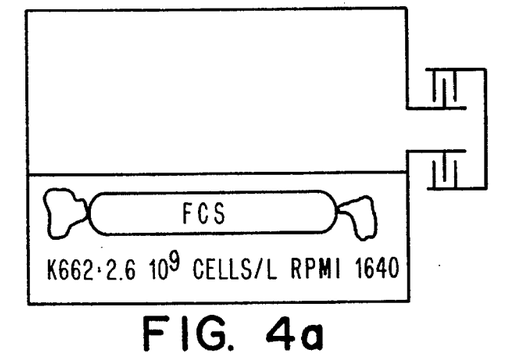
FIG. 4*a–c* shows: the purification steps: at (FIG. 4*a*) cell culture, at (FIG. 4*b*) the curve obtained after a MonoQ column, and at (FIG. 4*c*) the curve obtained after Superose 12. The active fractions lie in the hatched portions.
Figure 4B:
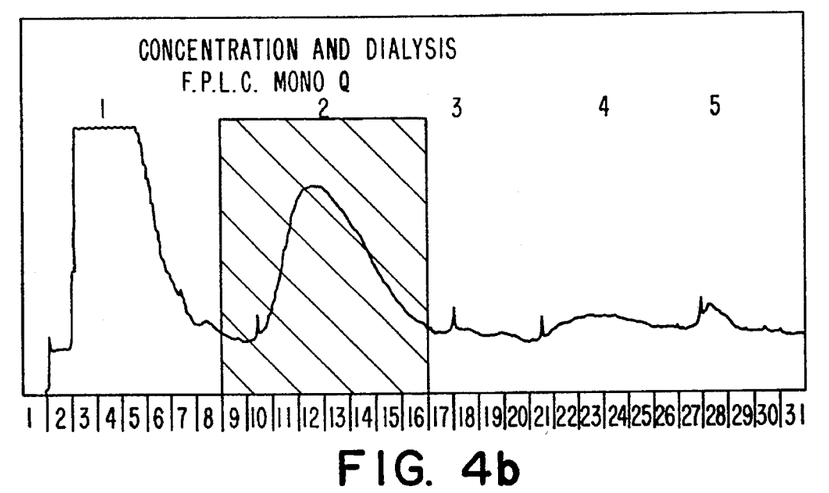
Figure 4C:
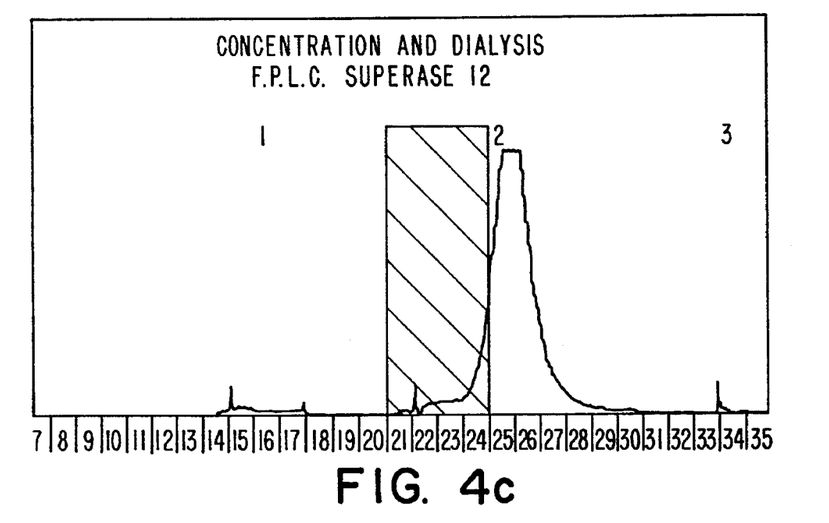

In column 4 at line 40, please begin a new paragraph with the phrase " FIG. 4a-c ".

In column 12 at line 61, column 13 at line 55, and column 14 at line 29, please delete "µof " and insert -- µl of --.

In column 17-18, Sequence Listing, please delete " 162 amino acids " and insert -- 163 amino acids --.

In column 19-20, Sequence Listing, fifth row, please insert " * -- " after the amino acid " Pro ".

Signed and Sealed this

Twenty-fifth Day of November, 1997

Attest:

BRUCE LEHMAN

Attesting Officer

Commissioner of Patents and Trademarks